US012741922B2

(12) United States Patent
Huang et al.

(10) Patent No.: US 12,741,922 B2
(45) Date of Patent: Sep. 22, 2026

(54) METHOD FOR PREPARING ACETIC ACID BY CATALYST

(71) Applicant: Taiyuan University of Technology, Taiyuan (CN)

(72) Inventors: Wei Huang, Taiyuan (CN); Shiqi Tao, Taiyuan (CN); Yongjun Liu, Taiyuan (CN); Qian Zhang, Taiyuan (CN); Ruijia Wang, Taiyuan (CN); Yin Tang, Taiyuan (CN)

(73) Assignee: Taiyuan University of Technology, Taiyuan (CN)

(*) Notice: Subject to any disclaimer, the term of this patent is extended or adjusted under 35 U.S.C. 154(b) by 601 days.

(21) Appl. No.: 18/224,584

(22) Filed: Jul. 21, 2023

(65) Prior Publication Data

US 2024/0083832 A1 Mar. 14, 2024

(30) Foreign Application Priority Data

Sep. 8, 2022 (CN) ........................ 202211092621.8

(51) Int. Cl.

| | |
|---|---|
| ***C07C 51/15*** | (2006.01) |
| ***B01J 23/44*** | (2006.01) |
| ***B01J 23/75*** | (2006.01) |
| ***B01J 37/06*** | (2006.01) |
| ***B01J 37/10*** | (2006.01) |
| ***B01J 37/16*** | (2006.01) |
| ***B01J 37/30*** | (2006.01) |
| *B01J 23/42* | (2006.01) |
| *B01J 23/89* | (2006.01) |
| *B01J 35/73* | (2024.01) |

(52) U.S. Cl.

CPC ............... *C07C 51/15* (2013.01); *B01J 23/44* (2013.01); *B01J 23/75* (2013.01); *B01J 37/06* (2013.01); *B01J 37/10* (2013.01); *B01J 37/16* (2013.01); *B01J 37/30* (2013.01); *B01J 23/42* (2013.01); *B01J 23/8913* (2013.01); *B01J 35/73* (2024.01)

(58) Field of Classification Search

None

See application file for complete search history.

(56) References Cited

U.S. PATENT DOCUMENTS

| | | | |
|---|---|---|---|
| 3,769,329 | A | 10/1973 | Paulik et al. |
| 5,364,963 | A | 11/1994 | Minami et al. |
| 5,773,642 | A | 6/1998 | Denis et al. |
| 7,368,598 | B2 | 5/2008 | Periana |

FOREIGN PATENT DOCUMENTS

| | | | | |
|---|---|---|---|---|
| EP | 2935184 B1 | | 3/2017 | |
| WO | WO-9959952 A1 | * | 11/1999 | ............. C07C 51/15 |

OTHER PUBLICATIONS

Tu ("Insight into Acetic Acid Synthesis from the Reaction of CH4 and CO2" ACS Catal. 2021, p. 3384) (Year: 2021).*

Shao ("Revealing the active sites of the structure Ni-based catalysts for one-step CO2/CH4 conversion into oxygenates by plasma-catalysis" Journal of CO2 Utilization, 2021, p. 101675) (Year: 2021).*

* cited by examiner

*Primary Examiner* — Amy C Bonaparte

(74) *Attorney, Agent, or Firm* — Nitin Kaushik

(57) ABSTRACT

A method for preparing acetic acid by catalyst including the following steps is provided, S1. preparing the hydrotalcite carrier by hydrothermal method; S2. ion exchange; S3. liquid phase reduction; S4. placing the CoPd/LDH catalyst obtained in S3 in a two-channel fixed bed step-by-step continuous reactor, carrying out the reaction at 100-400° C. and 0.1-20 MPa, synthesizing acetic acid by alternating feeding of $CH_4$+$H_2$+$H_2O$ and $CO_2$+$H_2$+$H_2O$, with the alternating time of 50-300 s. The present invention replaces the traditional process of acetic acid production including the steps of methane and carbon dioxide reforming to produce syngas. The process flow is short, the reaction conditions are mild, and the energy consumption and cost are greatly reduced.

9 Claims, No Drawings

METHOD FOR PREPARING ACETIC ACID BY CATALYST

CROSS REFERENCE TO THE RELATED APPLICATIONS

This application is based upon and claims priority to Chinese Patent Application No. 202211092621.8, filed on Sep. 8, 2022, the entire contents of which are incorporated herein by reference.

TECHNICAL FIELD

The present invention relates to the technical field of preparing acetic acid, and particularly relates to a method for preparing acetic acid by catalyst.

BACKGROUND ART

Acetic acid is an important product in the food industry and the largest organic acid in industrial production. It can be used in the production of acetic anhydride, vinyl acetate, alkyl acetate, and as a solvent for the synthesis of terephthalic acid. It is widely used in food, pharmaceutical, printing and dyeing industries. At present, 85% of acetic acid is produced by methanol carbonylation, the process includes high-temperature methane steam reforming to syngas, synthesis of methanol from syngas under high pressure conditions, and carbonylation of methanol and carbon monoxide to produce acetic acid. The production of syngas is an energy-intensive process, accounting for about 60% of the energy consumption of the entire process.

The invention patent U.S. Pat. No. 3,769,329 discloses a method for preparing acetic acid by methanol carbonylation in a homogeneous catalyst system with rhodium-based catalyst and methyl iodide as promoter. The reaction system contains a lot of water, which helps to increase the reaction rate, but leads to higher costs for the purification step of the product. The methanol carbonylation reaction of the invention patent U.S. Pat. No. 5,773,642 was carried out in the presence of a catalytic system containing at least one iridium compound and a halogenated promoter. Iridium-based catalysts have significant selectivity and generate very few by-products. This process is carried out in the presence of a relatively small amount of halogenated promoter, reducing the energy consumption required for the recovery of halogenated compounds. U.S. Pat. No. 5,364,963 provides a method for the production of acetic acid by methanol carbonylation using a rhodium-based catalyst. The rhodium complex in the rhodium-based catalyst is confined to the porous cross-linked vinyl pyridine resin, which reduces the loss of precious metals during the reaction and improves the stability of the catalyst. The invention patents U.S. Pat. Nos. 3,769,329, 5,773,642 and 5,364,963A are all methods for preparing acetic acid by methanol carbonylation process. However, the process of producing acetic acid by methanol carbonylation is multi-step, and the production cost of the whole process is higher. The invention patent EP 2935 184 B1 discloses an integrated process for the synthesis of acetic acid from syngas and dimethyl ether. This process simplifies the energy-intensive purification steps of methanol and carbon monoxide in the liquid phase carbonylation process, and eliminates the separation of precious metal complexes from corrosive liquid products. Compared with other methanol carbonylation processes, this process seems to be the most economical and feasible process. However, this process cannot avoid the most energy-intensive syngas production stage. Therefore, people seek a new method for the production of acetic acid. Reducing the production process of syngas and developing a new process for direct synthesis of acetic acid at low temperature of $CH_4$ can greatly reduce the production cost of acetic acid. U.S. Pat. No. 7,368,598 provides a process for the direct conversion of methane to acetic acid in the presence of a platinum group metal-based catalyst and an oxidant. According to 13C carbon-labeled isotope studies, two carbons in methane molecules can be directly converted into acetic acid products. Although the yield of acetic acid produced by this process is low, the process of direct synthesis of acetic acid from methane has broad application prospects.

As a greenhouse gas, $CO_2$ has a wide range of sources. The use of low-cost $CH_4$ and $CO_2$ to synthesize acetic acid can not only consume two greenhouse gases, but also greatly reduce the production cost of acetic acid. In addition, the reaction is a 100% atomic economy reaction, but the thermodynamics is unfavorable. How to work around the thermodynamic limitation of the reaction is the key to achieve efficient conversion of $CH_4$ and $CO_2$.

SUMMARY

The present invention provides a catalyst and preparation method with low cost, simple process and direct synthesis of acetic acid from $CH_4$ and $CO_2$ at low temperature.

To achieve the above purpose, the present invention provides a method for preparing acetic acid by catalyst, S1. preparing the hydrotalcite carrier by hydrothermal method: mixing $MgCl_2 \cdot 6H_2O$, $AlCl_3 \cdot 6H_2O$ and urea according to the molar ratio of 1-5:1-5:1-7 and dissolving them in methanol, after stirring evenly, sealing the product in a polytetrafluoroethylene lining, centrifuging the white precipitate obtained by hydrothermal method, washing with deionized water and ethanol, drying the product at 50-120° C. for 10-24 h, and obtaining hydrotalcite carrier MgAl-LDH;

S2. ion exchange: dispersing the MgAl-LDH obtained in S1 in deionized water containing metal salts, after stirring and exchanging, centrifuging the precipitate, collecting the centrifuged precipitate and washing it with water;

S3. liquid phase reduction: dispersing the precipitate after washed in S2 in $NaBH_4$ aqueous solution, after stirring and reducing for 0.1-2 h, washing it with deionized water and ethanol respectively, after drying, roasting in an inert atmosphere for 1-5 h, and obtaining CoPd/LDH catalyst;

S4. placing the CoPd/LDH catalyst obtained in S3 in a two-channel fixed bed step-by-step continuous reactor, carrying out the reaction at 100-400° C. and 0.1-20 MPa, synthesizing acetic acid by alternating feeding of $CH_4$+$H_2$+$H_2O$ and $CO_2$+$H_2$+$H_2O$, with the alternating time of 50-300 s.

Preferably, in S1, the temperature of the hydrothermal method is 100-200° C. and reaction time is 5-24 h.

Preferably, in S1, the molar ratio of Mg:Al in hydrotalcite carrier MgAl-LDH is 1-5:1-5.

Preferably, in S2, the metal salt is one or more of cobalt salt, palladium salt and platinum salt, and the exchange time is 1-5 h.

Preferably, in S2, cobalt salts include $K_3[Co(CN)_6]$.

Preferably, in S2, palladium salts include $Na_2PdCl_4$.

Preferably, in S2, platinum salts include $K_2PtCl_6$.

Preferably, in S3, the drying temperature is 50-120° C., the roasting temperature is 100-200° C., and the inert atmosphere is $N_2$, Ar and He.

Preferably, in S4, when $CH_4$+$H_2$+$H_2O$ and $CO_2$+$H_2$+$H_2O$ reaction gases are fed alternately, the flow rate are: the flow rate of $CO_2$ is 10-50 mL·min$^{-1}$, the flow rate of $CO_2$ mixed with $H_2$ was 5-20 mL·min$^{-1}$, and the flow rate of $CO_2$ mixed with $H_2O$ is 0-0.3 mL·min$^{-1}$, the flow rate of $CH_4$ is 10-50 mL·min$^{-1}$, the flow rate of $CH_4$ mixed with $H_2$ is 1-5 mL min$^{-1}$, and the flow rate of $CH_4$ mixed with $H_2O$ is 0-0.2 mL·min$^{-1}$.

The present invention has the following beneficial effects:

(1). $CH_4$ and $CO_2$ are both cheap and readily available greenhouse gases, which are both economical and environmentally friendly as raw materials.

(2). the invention replaces the expensive synthetic gas production step, the process flow is short and the reaction condition is mild, and the energy consumption and cost are greatly reduced.

(3). the invention has no methanol carbonylation process, does not require the use of toxic and corrosive iodine accelerators, is environmentally friendly, and the heterogeneous catalyst is easy to be separated and recovered from the reaction system, which can effectively reduce the cost of industrial production.

DETAILED DESCRIPTION OF THE EMBODIMENTS

The following is a complete and clear description of the content of the invention. The case described is part of the implementation case of the invention, not all implementation cases. The implementation cases in this invention and other implementation cases obtained by ordinary technicians in this field under the premise of no creative labor belong to the scope of protection of this invention.

Example 1

Dissolving $MgCl_2·6H_2O$, $AlCl_3·6H_2O$ and urea (molar ratio 3:1:7) in 30 mL methanol. Stirring the above mixture and moving it into the polytetrafluoroethylene lining, sealing, and hydrothermal reaction at 150° C. for 10 h, centrifuging the obtained white precipitate, washing them several times with deionized water and ethanol, drying 70° C. for 12 h, obtaining MgAl-LDH. Dispersing 1 g MgAl-LDH in 300 mL deionized water containing 0.5 mmol $K_3[Co(CN)_6]$ and stirring for 3 h, then adding 0.5 mmol $Na_2PdCl_4$ to the aqueous solution and stirring for 3 h, collecting the precipitate by centrifugation and washing with water for 3 times. Dispersing the fully washed precipitate in 300 mL freshly prepared $NaBH_4$ (20 mM) aqueous solution and stirring for 1 h to ensure complete reduction of metal ions. Collecting the final product, washing with deionized water and ethanol in turn, drying at 50° C., roasting at 150° C. $N_2$ atmosphere for 3 h (heating rate of 2° C.·min$^{-1}$), and obtaining CoPd/LDH catalyst after roasting. (Co: 3 wt. %, Pd: 5 wt. %)

Taking 0.5 g CoPd/LDH catalyst, and applying them to the direct synthesis of acetic acid from $CH_4$ and $CO_2$ in a fixed bed reactor.

The reaction conditions of acetic acid synthesis: the reaction pressure is atmospheric pressure; the reaction gas flow rates are: $CO_2$: 50 mL·min$^{-1}$, $CO_2$ mixed with $H_2$: 20 mL·min$^{-1}$; $CO_2$ mixed with $H_2O$: 0.1 mL·min$^{-1}$; $CH_4$: 50 mL·min$^{-1}$, $CH_4$ mixed with $H_2$: 5 mL·min$^{-1}$, $CH_4$ mixed with $H_2O$: 0.2 mL·min$^{-1}$. Obtaining the following results by changing the reaction temperature. When the reaction temperature is 100° C., the reaction results of the catalyst are as follows: the space-time yield of $CH_3OH$ is 2.55 mg·$g_{cat}^{-1}$·h$^{-1}$, and the space-time yield of $CH_3COOH$ is 3.09 mg·$g_{cat}^{-1}$·h$^{-1}$. When the reaction temperature is 150° C., the reaction results of the catalyst are as follows: the space-time yield of $CH_3OH$ is 4.97 mg·$g_{cat}^{-1}$·h$^{-1}$, and the space-time yield of $CH_3COOH$ is 4.04 mg·$g_{cat}^{-1}$·h$^{-1}$. When the reaction temperature is 200° C., the catalyst reaction results are: the space-time yield of $CH_3OH$ is 4.72 mg·$g_{cat}^{-1}$·h$^{-1}$, and the space-time yield of $CH_3COOH$ is 8.14 mg·$g_{cat}^{-1}$·h$^{-1}$. When the reaction temperature is 250° C., the catalyst reaction results: the space-time yield of $CH_3OH$ is 5.34 mg·$g_{cat}^{-1}$·h$^{-1}$, and the space-time yield of $CH_3COOH$ is 1.38 mg·$g_{cat}^{-1}$·h$^{-1}$.

Example 2

The preparation method of CoPd/LDH catalyst in this case is the same as that in example 1, the reaction conditions of direct synthesis of acetic acid from $CH_4$ and $CO_2$ in a fixed bed reactor are: the reaction temperature is 200° C.; the reaction pressure is atmospheric pressure; the reaction gas flow rates are: $CO_2$: 50 mL·min$^{-1}$, $CO_2$ mixed with $H_2$: 20 mL·min$^{-1}$, $CO_2$ mixed with $H_2O$: 0 mL·min$^{-1}$; $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 6.13 mg·$g_{cat}^{-1}$·h$^{-1}$, and the 0 space-time yield of $CH_3COOH$ is 1.51 mg·$g_{cat}^{-1}$·h$^{-1}$.

Example 3

The preparation method of CoPd/LDH catalyst in this example is the same as that in example 1, the reaction conditions of direct synthesis of acetic acid from $CH_4$ and $CO_2$ in a fixed bed reactor are: the reaction temperature is 200° C.; the reaction pressure is atmospheric pressure; the reaction gas flow rates are: $CO_2$: 50 mL·min$^{-1}$, $CO_2$ mixed with $H_2$: 20 mL·min$^{-1}$, $CO_2$ mixed with $H_2O$: 0.2 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are that the space-time yield of $CH_3OH$ is 5.34 mg·$g_{cat}^{-1}$·h$^{-1}$, and the space-time yield of $CH_3COOH$ is 4.19 mg·$g_{cat}^{-1}$·h$^{-1}$.

Example 4

The preparation method of CoPd/LDH catalyst in this example is the same as that in example 1, the reaction conditions of direct synthesis of acetic acid from $CH_4$ and $CO_2$ in a fixed bed reactor are: the reaction temperature is 200° C.; the reaction pressure is atmospheric pressure; the reaction gas flow rates are: $CO_2$: 50 mL·min$^{-1}$, $CO_2$ mixed with $H_2$: 20 mL·min$^{-1}$, $CO_2$ mixed with $H_2O$: 0.3 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 4.95 mg·$g_{cat}^{-1}$·h$^{-1}$, and the space-time yield of $CH_3COOH$ is 4.62 mg·$g_{cat}^{-1}$·h$^{-1}$.

Example 5

The preparation method of CoPd/LDH catalyst in this example is the same as that in example 1, the reaction conditions of direct synthesis of acetic acid from $CH_4$ and $CO_2$ in a fixed bed reactor are: the reaction temperature is 200° C.; the reaction pressure is atmospheric pressure; the reaction gas flow rates are: $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.1 mL·min$^{-1}$. The results of catalyst reaction are: the space-time yield of $CH_3OH$ is 6.34 mg·$g_{cat}^{-1}$·h$^{-1}$, and the space-time yield of $CH_3COOH$ is 2.15 mg·$g_{cat}^{-1}$·h$^{-1}$.

Example 6

The preparation method of CoPd/LDH catalyst in this example is the same as that in example 1, the reaction conditions of direct synthesis of acetic acid from $CH_4$ and $CO_2$ in a fixed bed reactor are: the reaction temperature is 200° C.; the reaction pressure is atmospheric pressure; the reaction gas flow rates are: the reaction gas flow rates are: $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0 mL·min$^{-1}$. The results of catalyst reaction are: the space-time yield of $CH_3OH$ is 7.14 mg·$g_{cat}^{-1}$·h$^{-1}$, and the space-time yield of $CH_3COOH$ is 1.19 mg·$g_{cat}^{-1}$·h$^{-1}$.

Example 7

Dissolving $MgCl_2 \cdot 6H_2O$, $AlCl_3 \cdot 6H_2O$ and urea (molar ratio 5:4:7) in 30 mL methanol. Stirring the above mixture and transferring into a polytetrafluoroethylene liner, sealing, and hydrothermal reaction at 100° C. for 20 h, centrifuging the obtained white precipitate, rinsing with deionized water and ethanol several times, and drying at 80° C. for 18 h to obtain MgAl-LDH. Dispersing 1 g MgAl-LDH in 300 mL deionized water containing 0.5 mmol $K_3[Co(CN)_6]$ and stirring for 1 h, then adding 0.5 mmol $Na_2PdCl_4$ to the aqueous solution and stirring for 5 h, collecting the precipitate by centrifugation and washing with water for 5 times. Dispersing the fully washed precipitate in 300 mL of $NaBH_4$ (20 mM) aqueous solution and stirring for 1.5 h to ensure the complete reduction of metal ions. Collecting the final product, washing them with deionized water and ethanol in turn, drying at 70° C., roasting at 120° C. $N_2$ atmosphere for 4 h (heating rate of 2° C.·min$^{-1}$), and obtaining CoPd/LDH catalyst after roasting. (Co: 3 wt. %, Pd: 5 wt. %)

Taking 0.5 g CoPd/LDH catalyst, and applying it to the direct synthesis of acetic acid from $CH_4$ and $CO_2$ in a fixed bed reactor. The reaction conditions are: the reaction temperature is 200° C.: the reaction pressure is atmospheric pressure; the reaction gas flow rates are: $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 2.96 mg·$g_{cat}^{-1}$·h$^{-1}$, and the space-time yield of $CH_3COOH$ is 3.81 mg·$g_{cat}^{-1}$·h$^{-1}$.

Example 8

Dissolving $MgCl_2 \cdot 6H_2O$, $AlCl_3 \cdot 6H_2O$ and urea (molar ratio 3:4:7) in 30 mL methanol. Stirring the above mixture and transferring into a polytetrafluoroethylene liner, sealing, and hydrothermal reaction at 100° C. for 20 h, centrifuging the obtained white precipitate, rinsing with deionized water and ethanol several times, and drying at 80° C. for 18 h to obtain MgAl-LDH. Dispersing 1 g MgAl-LDH in 300 mL deionized water containing 0.5 mmol $K_3[Co(CN)_6]$ and stirring for 5 h, then adding 0.5 mmol $Na_2PdCl_4$ to the aqueous solution and stirring for 1 h, collecting the precipitate by centrifugation and washing with water for one time.

Dispersing the fully washed precipitate in 300 mL of $NaBH_4$ (20 mM) aqueous solution and stirring for 0.8 h to ensure the complete reduction of metal ions. Collecting the final product, washing them with deionized water and ethanol in turn, drying at 110° C., roasting at 150° C. $N_2$ atmosphere for 2 h (heating rate of 2° C.·min$^{-1}$), and obtaining CoPd/LDH catalyst after roasting. (Co: 3 wt. %, Pd: 5 wt. %)

Taking 0.5 g CoPd/LDH catalyst, and applying it to the direct synthesis of acetic acid from $CH_4$ and $CO_2$ in a fixed bed reactor. The reaction conditions are: the reaction temperature is 200° C. the reaction pressure is atmospheric pressure; the reaction gas flow rates are $CO_2$: 50 mL·min$^{-1}$, $CO_2$ mixed with $H_2$: 20 mL·min, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 3.62 mg·$g_{cat}^{-1}$·h$^{-1}$, and the space-time yield of $CH_3COOH$ is 4.56 mg·$g_{cat}^{-1}$·h$^{-1}$.

Example 9

Dissolving $MgCl_2 \cdot 6H_2O$, $AlCl_3 \cdot 6H_2O$ and urea (molar ratio 2:4:7) in 30 mL methanol. Stirring the above mixture and transferring into a polytetrafluoroethylene liner, sealing, and hydrothermal reaction at 100° C. for 20 h, centrifuging the obtained white precipitate, rinsing with deionized water and ethanol several times, and drying at 80° C. for 18 h to obtain MgAl-LDH. Dispersing 1 g MgAl-LDH in 300 mL deionized water containing 0.5 mmol $K_3[Co(CN)_6]$ and stirring for 5 h, then adding 0.5 mmol $Na_2PdCl_4$ to the aqueous solution and stirring for 4 h, collecting the precipitate by centrifugation and washing with water for 2 times. Dispersing the fully washed precipitate in 300 mL of $NaBH_4$ (20 mM) aqueous solution and stirring for 1.6 h to ensure the complete reduction of metal ions. Collecting the final product, washing them with deionized water and ethanol in turn, drying at 60° C., roasting at 180° C. $N_2$ atmosphere for 4 h (heating rate of 2° C.·min$^{-1}$), and obtaining CoPd/LDH catalyst after roasting. (Co: 3 wt. %, Pd: 5 wt. %)

Taking 0.5 g CoPd/LDH catalyst, and applying them to the direct synthesis of acetic acid from $CH_4$ and $CO_2$ in a fixed bed reactor. The reaction conditions are: the reaction temperature is 200° C.; the reaction pressure is atmospheric pressure; the reaction gas flow rates are $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 2.54 mg·$g_{cat}^{-1}$·h$^{-1}$, and the space-time yield of $CH_3COOH$ is 7.36 mg·$g_{cat}^{-1}$·h$^{-1}$.

Example 10

Dissolving $MgCl_2 \cdot 6H_2O$, $AlCl_3 \cdot 6H_2O$ and urea (molar ratio 2:2:7) in 30 mL methanol. Stirring the above mixture and transferring into a polytetrafluoroethylene liner, sealing, and hydrothermal reaction at 100° C. for 24 h, centrifuging the obtained white precipitate, rinsing with deionized water and ethanol several times, and drying at 50° C. for 24 h to obtain MgAl-LDH. Dispersing 1 g MgAl-LDH in 300 mL deionized water containing 1 mmol $K_3[Co(CN)_6]$ and stirring for 1 h, collecting the precipitate by centrifugation and washing with water for one time, then dispersing the fully washed precipitate in 300 mL of $NaBH_4$ (20 mM), stirring for 2 h to ensure the complete reduction of metal ions. Collecting the final product, washing them with deionized water and ethanol in turn, drying at 120° C., roasting at 100°

C. $N_2$ atmosphere for 3 h (heating rate of 2° C.·min$^{-1}$), and obtaining Co/LDH catalyst after roasting. (Co: 6 wt. %)

Taking 0.5 g Co/LDH catalyst, and applying them to the direct synthesis of acetic acid from $CH_4$ and $CO_2$ in a fixed bed reactor. The reaction conditions are: the reaction temperature is 200° C.; the reaction pressure is atmospheric pressure; the reaction gas flow rates are $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 6.52 mg·g$_{cat}^{-1}$·h$^{-1}$, and the space-time yield of $CH_3COOH$ is 0.05 mg·g$_{cat}^{-1}$·h$^{-1}$.

Example 11

Dissolving $MgCl_2·6H_2O$, $AlCl_3·6H_2O$ and urea (molar ratio 4:3:7) in 30 mL methanol. Stirring the above mixture and transferring into a polytetrafluoroethylene liner, sealing, and hydrothermal reaction at 200° C. for 5 h, centrifuging the obtained white precipitate, rinsing with deionized water and ethanol several times, and drying at 120° C. for 10 h to obtain MgAl-LDH. Dispersing 1 g MgAl-LDH in 300 mL deionized water containing 1 mmol $Na_2PdCl_4$ and stirring for 5 h, collecting the precipitate by centrifugation and washing with water for 5 times, then dispersing the fully washed precipitate in 300 mL of $NaBH_4$ (20 mM), stirring for 0.1 h to ensure the complete reduction of metal ions. Collecting the final product, washing them with deionized water and ethanol in turn, drying at 100° C., roasting at 200° C. $N_2$ atmosphere for 1 h (heating rate of 2° C.·min$^{-1}$), and obtaining Pd/LDH catalyst after roasting. (Pd: 10 wt. %)

Taking 0.5 g Pd/LDH catalyst, and applying it to the direct synthesis of acetic acid from $CH_4$ and $CO_2$ in a fixed bed reactor. The reaction conditions are: the reaction temperature is 200° C.; the reaction pressure is 10 MPa; the reaction gas flow rates are $CO_2$: 50 mL·min$^{-1}$, $CO_2$ mixed with $H_2$: 20 mL·min$^{-1}$, $CO_2$ mixed with $H_2O$ 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL·min$^{-1}$. The results of catalyst reaction are: the space-time yield of $CH_3OH$ is 95.54 mg·g$_{cat}^{-1}$·h$^{-1}$, and the space-time yield of $CH_3COOH$ is 346.49 mg·g$_{cat}^{-1}$·h$^{-1}$.

Example 12

Dissolving $MgCl_2·6H_2O$, $AlCl_3·6H_2O$ and urea (molar ratio 1:5:7) in 30 mL methanol. Stirring the above mixture and transferring into a polytetrafluoroethylene liner, sealing, and hydrothermal reaction at 130° C. for 12 h, centrifuging the obtained white precipitate, rinsing with deionized water and ethanol several times, and drying at 90° C. for 12 h to obtain MgAl-LDH. Dispersing 1 g MgAl-LDH in 300 mL deionized water containing 1 mmol $K_2PtCl_6$ and stirring for 4 h, collecting the precipitate by centrifugation and washing with water for 3 times, then dispersing the fully washed precipitate in 300 mL of $NaBH_4$ (20 mM), stirring for 0.5 h to ensure the complete reduction of metal ions. Collecting the final product, washing them with deionized water and ethanol in turn, drying at 80° C., roasting at 130° C. $N_2$ atmosphere for 2 h (heating rate of 2° C.·min$^{-1}$), and obtaining Pt/LDH catalyst after roasting. (Pd: 16 wt. %)

Taking 0.5 g Pt/LDH catalyst, and applying them to the direct synthesis of acetic acid from $CH_4$ and $CO_2$ in a fixed bed reactor. The reaction conditions are: the reaction temperature is 200° C.; the reaction pressure is 15 MPa; the reaction gas flow rates are $CO_2$: 50 mL·min$^{-1}$, $CO_2$ mixed with $H_2$: 20 mL·min$^{-1}$, $CO_2$ mixed with $H_2O$: 0.1 mL·min$^{-1}$. $CH_4$: 50 mL·min$^{-1}$, $CH_4$ mixed with $H_2$: 5 mL·min$^{-1}$, $CH_4$ mixed with $H_2O$: 0.2 mL min$^{-1}$. The results of catalyst reaction are: the space-time yield of $CH_3OH$ is 43.29 mg·g$_{cat}^{-1}$·h$^{-1}$, and the space-time yield of $CH_3COOH$ is 130.85 mg·g$_{cat}^{-1}$·h$^{-1}$.

What is claimed is:

1. A method for preparing acetic acid by a catalyst, comprising:

S1: preparing a hydrotalcite carrier by a hydrothermal method, comprising: mixing $MgCl_2·6H_2O$, $AlCl_3·6H_2O$, and urea according to a molar ratio of (1-5):(1-5):(1-7) to obtain a resulting mixture and dissolving the resulting mixture in methanol to obtain a resulting solution, after stirring the resulting solution evenly, sealing a stirred solution in a polytetrafluoroethylene lining for a hydrothermal reaction, centrifuging a white precipitate obtained by the hydrothermal reaction, washing a centrifuged white precipitate with a first deionized water and a first ethanol, drying a washed white precipitate at 50-120° C. for 10-24 h to obtain a hydrotalcite carrier MgAl-LDH;

S2: an ion exchange process, comprising: dispersing the hydrotalcite carrier MgAl-LDH obtained in S1 in a deionized water containing a metal salt including a cobalt salt and a palladium salt stirring and performing ion exchange with the cobalt salt and the palladium salt to obtain an exchange solution, then centrifuging the exchange solution to obtain a centrifuged precipitate, collecting the centrifuged precipitate and washing the centrifuged precipitate with water to obtain a washed precipitate;

S3: a liquid phase reduction process, comprising: dispersing the washed precipitate obtained in S2 in a $NaBH_4$ aqueous solution, after stirring and reducing for 0.1-2 h to obtain a reduced solution, performing washing the reduced solution with a second deionized water and a second ethanol respectively to obtain a washed product, after drying the washed product to obtain a dried product, roasting the dried product in an inert atmosphere for 1-5 h to obtain a CoPd-supported MgAl-LDH catalyst; and S4: placing the CoPd-supported MgAl-LDH catalyst obtained in S3 in a two-channel fixed bed step-by-step continuous reactor, carrying out a reaction at 100-400° C. and 0.1-20 MPa, synthesizing the acetic acid by an alternating feeding of $CH_4$+$H_2$+$H_2O$ and $CO_2$+$H_2$+$H_2O$, with an alternating time of 50-300 s.

2. The method for preparing the acetic acid by the catalyst according to claim 1, wherein in S1, a temperature of the hydrothermal reaction is 100-200° C., and a reaction time is 5-24 h.

3. The method for preparing the acetic acid by the catalyst according to claim 1, wherein in S1, a molar ratio of Mg:Al in the hydrotalcite carrier MgAl-LDH is (1-5):(1-5).

4. The method for preparing the acetic acid by the catalyst according to claim 1, wherein in S2, an exchange time is 1-5 h.

5. The method for preparing the acetic acid by the catalyst according to claim 4, wherein in S2, the cobalt salt comprises $K_3$ [$Co(CN)_6$].

6. The method for preparing the acetic acid by the catalyst according to claim 4, wherein in S2, the palladium salt comprises $Na_2PdCl_4$.

7. The method for preparing the acetic acid by the catalyst according to claim 4, wherein in S2, the metal salt is-further comprises a platinum salt, and the platinum salt comprises $K_2PtCl_6$.

8. The method for preparing the acetic acid by the catalyst according to claim 1, wherein in S3, a drying temperature is 50-120° C., a roasting temperature is 100-200° C., and the inert atmosphere is $N_2$, Ar, and He.

9. The method for preparing the acetic acid by the catalyst according to claim 1, wherein in S4, when $CH_4+H_2+H_2O$ and $CO_2+H_2+H_2O$ reaction gases are fed alternately, flow rates are as follows: a flow rate of $CO_2$ is 10-50 $mL \cdot min^{-1}$, a flow rate of $CO_2$ mixed with $H_2$ is 5-20 $mL \cdot min^{-1}$, and a flow rate of $CO_2$ mixed with $H_2O$ is 0-0.3 $mL \cdot min^{-1}$, a flow rate of $CH_4$ is 10-50 $mL \cdot min^{-1}$, a flow rate of $CH_4$ mixed with $H_2$ is 1-5 $mL \cdot min^{-1}$, and a flow rate of $CH_4$ mixed with $H_2O$ is 0-0.2 $mL \cdot min^{-1}$.

* * * * *